US007820151B2

(12) United States Patent
de la Poterie et al.

(10) Patent No.: US 7,820,151 B2
(45) Date of Patent: *Oct. 26, 2010

(54) COMPOSITION FOR COATING KERATIN FIBERS, COMPRISING AT LEAST ONE TACKY WAX AND FIBERS

(75) Inventors: Valérie de la Poterie, Lailly-en-Val (FR); Florence Lahousse, Vitry sur Seine (FR); Thérèse Daubige, Beaumont en Véron (FR)

(73) Assignee: L'Oreal S.A., Paris (FR)

( * ) Notice: Subject to any disclaimer, the term of this patent is extended or adjusted under 35 U.S.C. 154(b) by 1534 days.

This patent is subject to a terminal disclaimer.

(21) Appl. No.: 11/056,239

(22) Filed: Feb. 14, 2005

(65) Prior Publication Data

US 2005/0215679 A1    Sep. 29, 2005

(30) Foreign Application Priority Data

Feb. 13, 2004    (FR) .................................. 04 50265

(51) Int. Cl.
    *A61Q 1/10*    (2006.01)
(52) U.S. Cl. ..................................... 424/70.7; 424/401
(58) Field of Classification Search .................. None
    See application file for complete search history.

(56) References Cited

U.S. PATENT DOCUMENTS

| 3,673,160 | A | 6/1972 | Buisson et al. |
| 3,802,841 | A | 4/1974 | Robin |
| 3,937,811 | A | 2/1976 | Papantoniou et al. |
| 4,887,622 | A | 12/1989 | Gueret |
| 5,159,052 | A | 10/1992 | Barthelemy et al. |
| 5,472,798 | A | 12/1995 | Kumazawa et al. |
| 5,756,635 | A | 5/1998 | Michaud et al. |
| 5,860,432 | A | 1/1999 | Gueret |
| 5,894,847 | A | 4/1999 | Gueret |
| 5,925,337 | A | 7/1999 | Arraudeau et al. |
| 5,934,292 | A | 8/1999 | Gueret |
| 6,103,221 | A | 8/2000 | Arnaud et al. |
| 6,258,916 | B1 | 7/2001 | Michaud et al. |
| 6,345,923 | B2 | 2/2002 | Gueret |
| 6,491,931 | B1 | 12/2002 | Collin |
| 2002/0031533 | A1 | 3/2002 | Afriat |
| 2002/0098217 | A1 | 7/2002 | Piot et al. |
| 2003/0086951 | A9 | 5/2003 | Piot et al. |
| 2004/0096473 | A1* | 5/2004 | Jager-Lezer ................ 424/401 |
| 2004/0137020 | A1 | 7/2004 | De La Poterie et al. |
| 2004/0137021 | A1 | 7/2004 | De La Poterie et al. |
| 2004/0142831 | A1 | 7/2004 | Jager Lezer |
| 2005/0172421 | A1* | 8/2005 | Jager-Lezer et al. ........... 8/405 |
| 2005/0188474 | A1* | 9/2005 | De La Poterie et al. ......... 8/404 |
| 2005/0191258 | A1* | 9/2005 | De La Poterie et al. .... 424/70.1 |
| 2005/0191262 | A1* | 9/2005 | De La Poterie et al. .. 424/70.11 |

FOREIGN PATENT DOCUMENTS

| EP | 0 360 708 B1 | 3/1990 |
| EP | 0 549 494 B1 | 6/1993 |
| EP | 0 611 170 B1 | 8/1994 |
| EP | 0 686 858 B1 | 12/1995 |
| EP | 0 811 336 B1 | 12/1997 |
| EP | 0 811 337 B1 | 12/1997 |
| EP | 0 842 620 B1 | 5/1998 |
| EP | 0 921 217 B1 | 6/1999 |
| EP | 1 157 683 A2 | 11/2001 |
| EP | 1 172 078 A2 | 1/2002 |
| EP | 1 201 221 B1 | 5/2002 |
| EP | 1 400 234 A1 | 3/2004 |
| EP | 1396257 * | 3/2004 |
| EP | 1396258 * | 3/2004 |
| EP | 1396259 * | 3/2004 |
| EP | 1 424 058 A1 | 6/2004 |
| FR | 2 079 785 | 11/1971 |
| FR | 2 232 303 | 1/1975 |
| FR | 2 607 373 A1 | 6/1988 |
| FR | 2 792 190 A1 | 10/2000 |
| FR | 2844 185 * | 3/2004 |
| FR | 2844710 * | 3/2004 |
| FR | 2844999 * | 4/2004 |
| JP | 2000/136110 | 5/2000 |
| JP | 2001/48750 | 2/2001 |
| JP | 2002/145739 | 5/2002 |
| WO | WO 91/12793 | 9/1991 |
| WO | WO 01/03653 | 1/2001 |

OTHER PUBLICATIONS

English translation of Notice of Reasons for Rejection mailed May 29, 2007, in the related Japanese Patent Application No. 2005-33677.
Leon M. Prince, "Microemulsions," Academic Press, Inc., pp. 21-32, (1977).
Kirk-Othmer, "Encyclopedia of Chemical Technology," Third Edition, vol. 22, John Wiley & Sons, pp. 332-432 (1983).
European Search Report No. EP 05 29 0253, Dated Apr. 28, 2005.
English language abstract of EP 1 172 078 A2, Jan. 16, 2002.
English language abstract of FR 2 792 190 A1, Oct. 20, 2000.
Masaki Okuyama, Recent research and development of mascara and eyeliner, Fragrance Journal, 1997, vol. 25, No. 8, pp. 58-64.
Abstract for Masaki Okuyama, Recent research and development of mascara and eyeliner, Fragrance Journal, 1997, vol. 25, No. 8, p. 58, Abstract.

(Continued)

*Primary Examiner*—Jyothsna A Venkat
(74) *Attorney, Agent, or Firm*—Finnegan, Henderson, Farabow, Garrett & Dunner, LLP

(57) ABSTRACT

Disclosed herein is a composition for coating keratin fibers, comprising, in a cosmetically acceptable medium, at least one tacky wax and fibers, wherein the at least one tacky wax may have a tack of greater than or equal to 0.7 N.s and a hardness of less than or equal to 3.5 MPa. Also disclosed herein are methods of using this composition and an assembly comprising this composition.

24 Claims, 1 Drawing Sheet

OTHER PUBLICATIONS

R. Pigeon et al., "Chimie Macromoléculaire Appliquée," vol. 40/41, No. 600, pp. 139-158 (1974).

Summary of R. Pigeon et al., "Chimie Macromoléculaire Appliquée," vol. 40/41, No. 600, pp. 139-140 (1974), Abstract.

* cited by examiner

COMPOSITION FOR COATING KERATIN FIBERS, COMPRISING AT LEAST ONE TACKY WAX AND FIBERS

The present disclosure relates to a cosmetic composition for coating keratin fibers, comprising at least one "tacky" wax and fibers. The present disclosure also relates to a cosmetic process for making up or treating keratin fibers such as the eyelashes, the eyebrows and the hair.

The present disclosure further relates to a care or makeup composition for the eyes, such as an eyeliner and an eyeshadow.

The composition disclosed herein may be a makeup composition for keratin fibers, a makeup base for keratin fibers, or base coat, a composition to be applied onto a makeup, also known as a top coat, or a composition for treating keratin fibers. For example, the composition disclosed herein can be a mascara.

As used herein, the term "mascara" means a composition intended to be applied to the eyelashes: it can be a makeup composition for the eyelashes, a makeup base for the eyelashes, a composition to be applied onto a mascara, also known as a top coat, or a cosmetic treatment composition for the eyelashes. The mascara is, for example, intended for the eyelashes of human beings, but also for false eyelashes.

Mascaras are commonly prepared according to two types of formulation: water-based mascaras, known as cream mascaras, in the form of an emulsion of waxes in water; and anhydrous mascaras or mascaras with a low water content, known as waterproof mascaras, in the form of dispersions of waxes in organic solvents.

It is known practice to use various waxes to formulate mascaras, for instance those described in document WO-A-91/12793, for example, beeswax, candelilla wax, carnauba wax or polyethylene wax.

However, when the mascaras contain certain waxes in high content (such as in a content of greater than 10%), for instance carnauba wax, rice bran wax or polyethylene wax, the makeup of the eyelashes obtained may look grainy, thus giving a non-smooth and non-uniform makeup result, these defects rendering the makeup result unattractive.

Moreover, to obtain a mascara with good charging properties, i.e., to obtain heavy makeup of the eyelashes, it is possible to incorporate into the mascara one or more waxes in a total content of greater than 25% by weight relative to the total weight of the mascara. However, by using conventional waxes such as beeswax, candelilla wax or carnauba wax at these high contents, the mascara composition may acquire a very thick consistency, or even become too compact, and cannot be applied easily to the eyelashes with the mascara brush applicators commonly used. The excessively thick mascara may be deposited on the eyelashes in the form of lumps and the makeup result thus obtained may not have the desired smooth appearance; the makeup result may not be uniform and may look unattractive.

In addition, certain waxes such as orange wax or lanolin wax, used at contents of greater than 25% by weight, may lead to compositions that are not sufficiently stable, such as after storage for two weeks at room temperature (25° C.), the composition may set to a solid (substantial increase in viscosity) or undergoe a phase separation that may be seen with the naked eye. The composition may then be unsuitable for application to the eyelashes.

Another property desired in mascara is lengthening of the eyelashes. To obtain such an effect, it is known practice to use fibers as additives.

However, the known cosmetic compositions containing fibers may have a certain number of drawbacks; such as non-uniform and poorly charging (poorly volumizing) makeup. For example, the known mascara compositions containing fibers may not allow an optimum lengthening effect to be obtained on the eyelashes after application of the composition, either on account of poor orientation and a random distribution of the fibers on the eyelashes (which do not lie in the continuation of the eyelashes), or on account of poor attachment to the eyelashes, since the fibers may slide on the eyelashes and, leading to only a small amount of fibers and product being deposited on the support.

The effect obtained by the known mascara compositions containing fibers may thus be often aesthetically unacceptable, for example, in the case of dense, long and/or curled eyelashes, for which an unattractive "Christmas tree" appearance of the eyelashes may be obtained, with a non-smooth appearance of the eyelashes.

Another major drawback associated with the use of fibers in the known compositions is the difficulty in obtaining a volumizing (charging) effect, since the attachment of the product to the eyelashes may be countered by the sliding of the fibers on the surface of the eyelashes.

Disclosed herein is a composition for coating keratin fibers, making it possible to obtain a smooth, uniform makeup result on the keratin fibers, with good, charging distribution of the fibers along the eyelashes.

The present inventors have discovered that such a composition may be obtained by using at least one wax that has tacky properties (high tack) and fibers. The at least one wax can lead to a composition for coating keratin fibers, such as a mascara, that can apply easily to the eyelashes, show good attachment to the eyelashes and lead to the formation of a smooth, uniform makeup result with a lengthening and charging (volumizing) effect on the eyelashes.

Disclosed herein is a composition for coating keratin fibers, comprising, in a cosmetically acceptable medium, at least one tacky wax with a tack of greater than or equal to 0.7 N.s and, for example, a hardness of less than or equal to 3.5 MPa, and fibers.

Also disclosed herein is a non-therapeutic cosmetic makeup or care process for keratin fibers, such as the eyelashes, comprising applying to the keratin fibers a composition as defined herein.

Further disclosed herein is the use of a composition as defined herein to obtain a uniform and/or smooth makeup result on keratin fibers, such as the eyelashes, and a good lengthening effect on made-up keratin fibers and/or a volumizing effect.

Even further disclosed herein is the use of the combination of at least one tacky wax with a tack of greater than or equal to 0.7 N.s and, for example, a hardness of less than or equal to 3.5 MPa, and fibers, in a composition for making up keratin fibers, to obtain a uniform and/or smooth makeup result on the keratin fibers, and a lengthening and/or volumizing effect on made-up keratin fibers.

As used herein, the term "cosmetically acceptable medium" means a cosmetic medium that is compatible with the eyelashes or the skin.

1) Tacky wax

Figure 1:
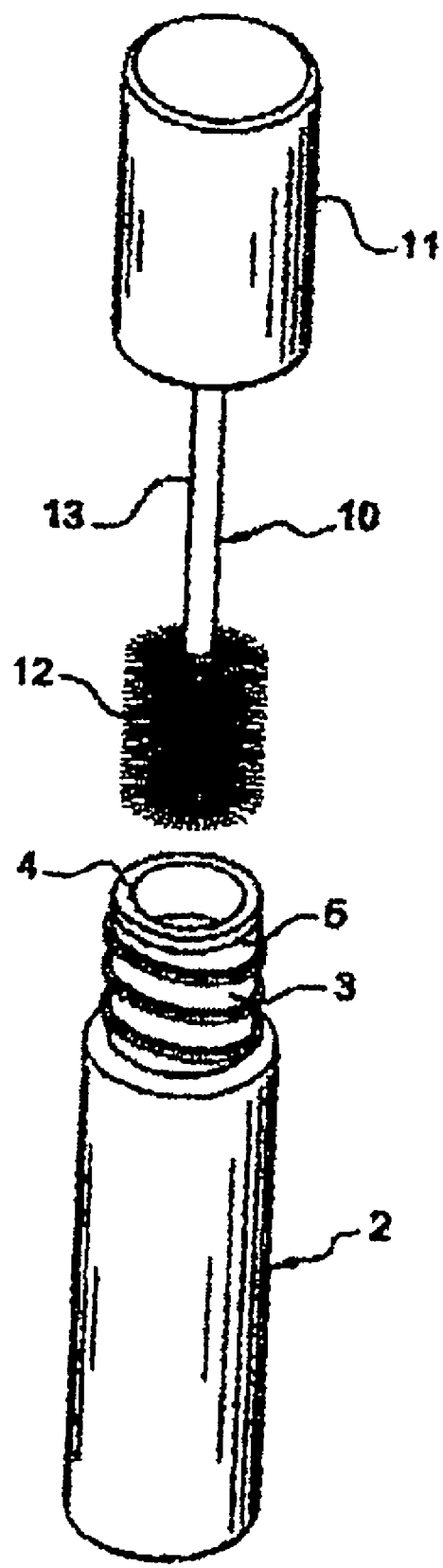
FIG. 1 is a respresentation of a packaging and applicator assembly for coating keratin fibers as disclosed herein.

As used herein, the term "wax" means a lipophilic fatty compound that is solid at room temperature (25° C.) and atmospheric pressure (760 mmHg, i.e., $10^5$ Pa), with a reversible solid/liquid change of state, having a melting point of greater than 30° C. such as greater than 55° C., up to 120° C., even up to 200° C.

By bringing the wax to its melting point, it is possible to make it miscible with oils and to form a microscopically homogeneous mixture, but on cooling the mixture to room temperature, recrystallization of the wax in the oils of the mixture is obtained.

As disclosed herein, the melting point is the temperature of the most endothermic peak observed by thermal analysis (Differential Scanning Calorimetry) as described in ISO standard 11357-3; 1999. The melting point of the wax may be measured using a differential scanning calorimeter (DSC), for example the calorimeter sold under the name "MDSC 2920" by the company TA Instruments.

The measurement protocol is as follows:
a sample of 5 mg of wax placed in a crucible is subjected to a first temperature increase ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 0.5° C./minute. During the second temperature increase, the variation of the difference in power absorbed by the empty crucible and by the crucible containing the sample of product is measured as a function of the temperature. The melting point of the compound is the temperature value corresponding to the top of the peak of the curve representing the variation in the difference in absorbed power as a function of the temperature.

The at least one tacky wax disclosed herein has a tack of greater than or equal to 0.7 N.s, for example, ranging from 0.7 N.s to 30 N.s; such as greater than or equal to 1 N.s, for example, ranging from 1 N.s to 20 N.s; further such as greater than or equal to 2 N.s, ranging, for example, from 2 to 10 N.s, and further, for example, from 2 N.s to 5 N.s.

The at least one tacky wax disclosed herein may have, for example, a hardness of less than or equal to 3.5 MPa, ranging, for example, from 0.01 to 3.5 MPa, such as from 0.05 MPa to 3 MPa, and further such as from 0.1 MPa to 2.5 MPa.

The tack of the wax is measured at 20° C. using the texturometer sold under the name TA-XT2i by the company Rheo, equipped with an acrylic polymer spindle in the form of a cone forming an angle of 45°, by measuring the change in force (compression force or stretching force) (F) as a function of time, during the following operation:

The spindle is displaced at a speed of 0.5 mm/s and then penetrates into the wax to a penetration depth of 2 mm. When the spindle has penetrated the wax to a depth of 2 mm, the spindle is held stationary for 1 second (corresponding to the relaxation time) and is then withdrawn at a speed of 0.5 mm/s. During the relaxation time, the force (compression force) decreases greatly until it becomes zero, and then, during the withdrawal of the spindle, the force (stretching force) becomes negative before rising again to the value 0. Tack corresponds to the integral of the curve of the force as a function of time for the portion of the curve corresponding to the negative force values (stretching force). The tack value is expressed in N.s.

To measure the tack of the wax, the wax is melted at a temperature equal to the melting point of the wax +10° C. The molten wax is poured into a container 25 mm in diameter and 20 mm deep. The wax is recrystallized at room temperature (25° C.) for 24 hours such that the surface of the wax is flat and smooth, and the wax is then kept for at least 1 hour at 20° C. before measuring the tack.

The hardness is determined by measuring the compression force, which is measured at 20° C. using the texturometer sold under the name TA-XT2i by the company Rheo, equipped with a cylindrical stainless-steel spindle 2 mm in diameter, by measuring the change in force (compression force or stretching force) (F) as a function of time, during the following operation:

The spindle is displaced at a speed of 0.1 mm/s and then penetrates into the wax to a penetration depth of 0.3 mm. When the spindle has penetrated the wax to a depth of 0.3 mm, the spindle is held stationary for 1 second (corresponding to the relaxation time) and is then withdrawn at a speed of 0.1 mm/s. During the relaxation time, the force (compression force) decreases greatly until it becomes zero, and then, during the withdrawal of the spindle, the force (stretching force) becomes negative before rising again to the value 0. The hardness corresponds to the maximum compression force measured between the surface of the spindle and the wax at the moment that they come into contact. The value of this force is expressed in MPa.

To measure the hardness, the wax is melted at a temperature equal to the melting point of the wax +20° C. The molten wax is poured into a container 30 mm in diameter and 20 mm deep. The wax is recrystallized at room temperature (25° C.) for 24 hours and is then stored for at least 1 hour at 20° C. before measuring the hardness.

The at least one tacky wax disclosed herein is chosen, for example, from $C_{20}$-$C_{40}$ alkyl(hydroxystearoyloxy)stearates.

Such tacky waxes are, for example, sold under the names "Kester Wax K 82 P" and "Kester Wax K 80 P" by the company Koster Keunen.

The at least one tacky wax may be in the form of an aqueous microdispersion of wax particles. As used herein, the term "aqueous microdispersion of wax" means an aqueous dispersion of wax particles in which the mean size of the wax particles is less than or equal to about 1 μm, wherein the mean size of the wax particles can readily be measured by one of ordinary skill in the art using known techniques.

Wax microdispersions are stable dispersions of colloidal wax particles, and are described, for example, in "Microemulsions Theory and Practice", L. M. Prince Ed., Academic Press (1977) pages 21-32.

For example, these wax microdispersions may be obtained by melting the wax in the presence of a surfactant, and optionally of a portion of water, followed by gradual addition of hot water with stirring. The intermediate formation of an emulsion of the water-in-oil type is observed, followed by a phase inversion, with final production of a microemulsion of the oil-in-water type. On cooling, a stable microdispersion of solid wax colloidal particles is obtained.

The wax microdispersions may also be obtained by stirring the mixture of wax, surfactant and water using stirring tools such as ultrasound, a high-pressure homogenizer or turbomixers.

The particles of the wax microdispersion have, for example, mean sizes of less than 1 μm, for example, ranging from 0.02 μm to 0.99 μm, such as less than 0.5 μm, for example, ranging from 0.06 μm to 0.5 μm.

These particles comprise a wax or a mixture of waxes. However, they may comprise a small proportion of oily and/or pasty fatty additives, a surfactant and/or a common liposoluble additive/active agent.

The at least one tacky wax may be present in the composition disclosed herein in an amount ranging, for example, from 0.5% to 65% by weight, such as from 5% to 60% by weight and further such as from 10% to 40% by weight, relative to the total weight of the composition.

For example, the at least one tacky wax may be present in the composition disclosed herein in an amount of greater than or equal to 25% by weight, such as from 25% to 60% by weight; for example, greater than or equal to 27% by weight, such as from 27% to 50% by weight; further, for example, greater than or equal to 28% by weight, such as from 28% to 45% by weight; and even further, for example, greater than or equal to 30% by weight, such as from 30% to 40% by weight, relative to the total weight of the composition.

2) Fibers

As used herein, the term "fiber" means an object of length L and diameter D such that L is greater than D, wherein D is the diameter of the circle in which the cross section of the fiber is inscribed. For example, the ratio L/D (or shape factor) is chosen ranging, for example, from 3.5 to 2,500, such as from 5 to 500 and further such as from 5 to 150.

The fibers that may be used in the composition disclosed herein may be mineral or organic fibers of synthetic or natural origin. They may be short or long, individual or organized, for example, braided, and hollow or solid. They may have any shape, and may, for example, have a circular or polygonal (square, hexagonal or octagonal) cross section, depending on the intended specific application. For example, the ends of the fibers are blunt and/or polished to prevent injury.

The fibers have a length ranging, for example, from 1 µm to 10 mm, such as from 0.1 mm to 5 mm and further such as from 0.3 mm to 3 mm. Their cross section may be within a circle of diameter ranging, for example, from 2 nm to 500 µm, such as from 100 nm to 100 µm and further such as from 1 µm to 50 µm. The weight or yarn count of the fibers is often given in denier or decitex (dtex), and represents the weight in grams per 9 km of yarn. For example, the fibers as disclosed herein may have a yarn count ranging from 0.01 to 10 denier, such as from 0.1 to 2 denier and further such as from 0.3 to 0.7 denier.

The fibers can be those used in the manufacture of textiles, such as silk fiber, cotton fiber, wool fiber, flax fiber, cellulose fiber extracted, for example, from wood, legumes or algae; rayon fiber, polyamide (Nylon®) fiber, viscose fiber, acetate fiber, such as rayon acetate fiber, acrylic polymer fiber, for example, polymethyl methacrylate fiber and poly(2-hydroxyethyl methacrylate) fiber; polyolefin fiber such as polyethylene fiber and polypropylene fiber; glass fiber, silica fiber, carbon fiber, such as in graphite form, polytetrafluoroethylene (such as Teflon®) fiber, insoluble collagen fiber, polyester fiber, polyvinyl chloride fiber and polyvinylidene chloride fiber, polyvinyl alcohol fiber, polyacrylonitrile fiber, chitosan fiber, polyurethane fiber, polyethylene phthalate fiber, and fibers formed from a mixture of polymers such as those mentioned above, for instance polyamide/polyester fibers.

In one embodiment, the fibers are polyamide (Nylon®) fibers.

The fibers used in surgery may also be used, for instance the resorbable synthetic fibers prepared from glycolic acid and caprolactone (Monocryl from Johnson & Johnson); resorbable synthetic fibers of the type which is a copolymer of lactic acid and of glycolic acid (Vicryl from Johnson & Johnson); polyterephthalic ester fibers (Ethibond from Johnson & Johnson) and stainless steel threads (Acier from Johnson & Johnson).

Moreover, the fibers may, for example, be surface-treated, and may, for example, be coated with a protective coat. As coated fibers that may be used herein, mention may be made, for example, of polyamide fibers coated with copper sulphide to give an anti-static effect (for example R-STAT from Rhodia) or another polymer enabling a particular organization of the fibers (specific surface treatment). Mention may also be made, for example, of fibers coated with mineral or organic pigments, such as the pigments mentioned below.

Fibers of synthetic origin, for example, organic fibers, such as those used in surgery, may, for example, be used.

The fibers that may also be used in the composition disclosed herein are, for example, polyamide fibers, cellulose fibers or polyethylene fibers. Their length (L) may range, for example, from 0.1 mm to 5 mm such as from 0.25 mm to 1.6 mm, and their mean diameter may range, for example, from 1 µm to 50 µm. In various embodiments, the polyamide fibers sold by Etablissements P. Bonte under the name "Polyamide 0.9 Dtex 3 mm", having a mean diameter of 6 µm, a yarn count of 0.9 dtex and a length ranging from 0.3 mm to 5 mm, or the polyamide fibers sold under the name Fiberlon 931-D1-S by the company LCW, having a yarn count of 0.9 dtex and a length of 0.3 mm, may be used. Cellulose (or rayon) fibers with a mean diameter of 50 µm and a length ranging from 0.5 mm to 6 mm may also be used, for instance those sold under the name "Natural rayon flock fiber RC1 BE-N003-M04" by the company Claremont Flock. Polyethylene fibers, for instance those sold under the name "Shurt Stuff 13 099 F" by the company Mini Fibers, may also be used.

Elastomeric fibers may also be used. As disclosed herein, the elastomeric fibers are fibers-which, when subjected to a stretching stress, strech, for example, of 30% relative to their initial length, return to a length substantially identical to their initial length when the stress is removed. The elastomeric fibers that may be mentioned include, for example, polyurethane fibers such as elastane (or Spandex®), fibers comprising at least 85% by weight of segmented polyurethane, such as Lycra® sold by Dupont de Nemours, elastodiene, or alternatively rubbery fibers obtained from natural rubber. These elastomeric fibers may, for example, be vulcanized.

The composition as disclosed herein may also comprise "rigid" fibers, as opposed to the fibers mentioned above, which are not rigid fibers.

The rigid fibers, which are initially substantially straight, when placed in a dispersing medium, do not undergo a substantial change in shape, which is reflected by the angular condition defined below, reflecting a shape that may be described as still substantially straight and linear. This angle condition reflects the stiffness of the fibers, as it is difficult to express by another parameter for objects that are as small as the rigid fibers.

The stiffness of the fibers is reflected by the following angular condition: for example, at least 50%, such as at least 75% and further such as at least 90%, in numerical terms, of the fibers are such that the angle formed between the tangent to the longitudinal central axis of the fiber and the straight line connecting the end to the point on the longitudinal central axis of the fiber corresponding to half the length of the fiber is less than 15°, and the angle formed between the tangent to the longitudinal central axis of the fiber at a point half way along the fiber and the straight line connecting one of the ends to the point on the longitudinal central axis of the fiber corresponding to half the length of the fiber, is less than or equal to 15° for the same fiber length ranging from 0.8 mm to 5 mm, such as from 1 mm to 4 mm, further such as from 1 mm to 3 mm, and even further such as 2 mm.

The angle mentioned above is, for example, measured at the two ends of the fiber and at a point half way along the fiber; in other words, three measurements are taken in this case and the average of the measured angles is less than or equal to 15°.

The tangent, at any point on the fiber, forms, for example, an angle of less than 15°.

As disclosed herein, the angle formed by the tangent at a point on the fiber is the angle formed between the tangent to the longitudinal central axis of the fiber at the point on the fiber and the straight line connecting the end of the fiber that is closest to the point to the point on the longitudinal central axis of the fiber corresponding to half the length of the fiber.

Generally, the rigid fibers that may be used in the composition disclosed herein have the same or substantially the same fiber length.

More specifically, when a medium in which are dispersed the rigid fibers to a fiber concentration of 1% by weight is observed by microscope, with an objective lens allowing a magnification of 2.5 and with full-field vision, a numerical majority of the rigid fibers, i.e., at least 50% numerically of the rigid fibers, such as at least 75% numerically of the rigid fibers and further such as at least 90% numerically of the rigid fibers, should satisfy the angular condition defined above. The measurement leading to the angle value is performed for the same length of fibers, ranging from 0.8 mm to 5 mm, such as from 1 to 4 mm, further such as from 1 to 3 mm, and even further such as 2 mm.

The medium in which the observation is performed is a dispersing medium that ensures good dispersion of the rigid fibers, for example, water or an aqueous gel of clay or of associative polyurethane. A direct observation of the composition containing the rigid fibers may also be performed. A sample of the prepared composition or dispersion is placed between a slide and cover slip for observation by microscope with an objective lens allowing a magnification of 2.5 and with full-field vision. Full-field vision allows the fibers to be viewed in their entirety.

The rigid fibers may be chosen from fibers of at least one synthetic polymer chosen from polyesters, polyurethanes, acrylic polymers, polyolefins, polyamides, such as non-aromatic polyamides, and aromatic polyimideamides.

Examples of rigid fibers that may be mentioned include:

polyester fibers, such as those obtained by chopping yarns sold under the names Fiber 255-100-R11-242T Taille 3 mm (eight-lobed cross section), Fiber 265-34-R11-56T Taille 3 mm (round cross section) and Fiber Coolmax 50-34-591 Taille 3 mm (four-lobed cross section) by the company Dupont de Nemours;

polyamide fibers, such as those sold under the names Trilobal Nylon 0.120-1.8 DPF; Trilobal Nylon 0.120-18 DPF; Nylon 0.120-6 DPF by the company Cellusuede products; or obtained by chopping yarns sold under the name Fiber Nomex Brand 430 Taille 3 mm by the company Dupont de Nemours;

polyimideamide fibers, such as those sold under the names "Kermel" and "Kermel Tech" by the company RHODIA;

poly(p-phenyleneterephthalamide) (or aramide) sold, for example, under the name Kevlar® by the company Dupont de Nemours;

fibers with a multilayer structure comprising alternating layers of polymers chosen from polyesters, acrylic polymers and polyamides, such as those described in documents EP-A-6 921 217, EP-A-686 858 and U.S. Pat. No. 5,472,798. Such fibers are sold under the names "Morphotex" and "Teijin Tetron Morphotex" by the company Teijin.

In one embodiment, the rigid fibers are chosen from aromatic polyimideamide fibers.

Polyimideamide yarns or fibers that may be used for the compositions disclosed herein are described, for example, in the document by R. Pigeon and P. Allard, Chimie Macromoléculaire Appliquée, 40/41 (1974), pages 139-158 (No. 600), or in U.S. Pat. No. 3,802,841 and documents FR-A-2 079 785, EP-A1-0 360 728 and EP-A-0 549 494.

For example, the aromatic polyimideamide fibers are chosen from polyimideamide fibers comprising repeating units of formula:

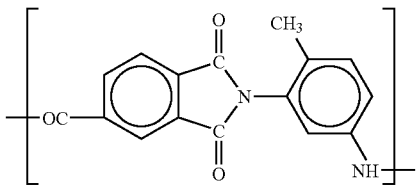

obtained by polycondensation of tolylene diisocyanate and trimellitic anhydride.

The fibers may be present in the composition disclosed herein in an amount ranging, for example, from 0.05% to 10% by weight, such as from 0.1% to 5% by weight and further such as from 0.3% to 3% by weight, relative to the total weight of the composition.

The composition as disclosed herein may further comprise at least one additional wax other than the tacky wax.

The at least one additional wax that may be used in the compositions disclosed herein are chosen from waxes that are solid and rigid at room temperature, of animal, plant, mineral or synthetic origin, and mixtures thereof.

The at least one additional wax may also have a hardness ranging from 0.05 MPa to 30 MPa such as from 6 MPa to 15 MPa, wherein the hardness is determined by the method mentioned above for the tacky wax.

The at least one additional wax that may be used include, for example, hydrocarbon-based waxes such as beeswax, lanolin wax and Chinese insect waxes; rice wax, carnauba wax, candelilla wax, ouricury wax, esparto grass wax, cork fiber wax, sugar cane wax, Japan wax and sumach wax; montan wax, microcrystalline waxes, paraffins and ozokerite; polyethylene waxes, the waxes obtained by Fisher-Tropsch synthesis and waxy copolymers, and also esters thereof.

Mention may also be made, for example, of the waxes obtained by catalytic hydrogenation of animal or plant oils comprising at least one fatty chain chosen from linear and branched $C_8$-$C_{32}$ fatty chains.

Among these Waxes, mention may be made, for example, of hydrogenated jojoba oil, isomerized jojoba oil such as the partially hydrogenated isomerized jojoba oil manufactured or sold by the company Desert Whale under the commercial reference Iso-Jojoba-50®, hydrogenated sunflower oil, hydrogenated castor oil, hydrogenated coconut oil and hydrogenated lanolin oil, bis(1,1,1-trimethylolpropane)tetrastearate sold under the name "Hest 2T-4S" by the company Heterene and bis(1,1,1-trimethylolpropane) tetrabehenate sold under the name Hest 2T-4B by the company Heterene.

Mention may also be made, for example, of silicone waxes and fluoro waxes.

It is also possible to use the wax obtained by hydrogenation of olive oil esterified with stearyl alcohol, sold under the name "Phytowax Olive 18 L 57" or the waxes obtained by hydrogenation of castor oil esterified with cetyl alcohol, sold under the name "Phytowax ricin 16L64 and 22L73" by the company Sophim. Such waxes are described in French patent application FR-A-2 792 190.

The at least one additional wax may also be present in the form of a wax microdispersion as described above for the tacky wax.

The at least one additional wax may be present in the composition disclosed herein in an amount ranging, for example, from 0.1% to 50% by weight, such as from 0.5% to 30% by weight and further such as from 1% to 20% by weight, relative to the total weight of the composition.

Cosmetically Acceptable Medium

The cosmetically acceptable medium of the composition may comprise at least one volatile solvent chosen, for example, from the volatile organic solvents and volatile oils defined below, and mixtures thereof.

The composition as disclosed herein may comprise an aqueous medium, constituting an aqueous phase, which may form the continuous phase of the composition.

The aqueous phase may comprise water or a mixture of water and at least one water-miscible solvent (water miscibility of greater than 50% by weight at 25° C.), for instance lower monoalcohols comprising from 1 to 5 carbon atoms, such as ethanol and isopropanol, glycols comprising from 2 to 8 carbon atoms, such as propylene glycol, ethylene glycol, 1,3-butylene glycol and dipropylene glycol, $C_3$-$C_4$ ketones and $C_2$-$C_4$ aldehydes.

The aqueous phase (water and optionally the water-miscible organic solvent) may be present in an amount ranging, for example, from 1% to 95% by weight, such as from 3% to 80% by weight, further such as from 5% to 60% by weight, relative to the total weight of the composition.

The composition as disclosed herein may also comprise at least one oil or organic solvent that may, for example, form a fatty phase, such as a continuous fatty phase. The composition may, for example, be an anhydrous composition.

As used herein, the term "volatile oil or organic solvent" means any non-aqueous medium that can evaporate on contact with the keratin fiber in less than one hour at room temperature and atmospheric pressure. The at least one volatile organic solvent and the at least one volatile oil as disclosed herein are volatile cosmetic organic solvents and oils, that are liquid at room temperature, having a non-zero vapor pressure at room temperature and atmospheric pressure, ranging from 0.13 Pa to 40 000 Pa ($10^{-3}$ to 300 mmHg), such as from 1.3 Pa to 13 000 Pa (0.01 to 100 mmHg) and further such as from 1.3 Pa to 1 300 Pa (0.01 to 10 mmHg). The term "non-volatile oil" means an oil that remains on the keratin fiber at room temperature and atmospheric pressure for at least several hours and has, for example, a vapor pressure of less than $10^{-3}$ mmHg (0.13 Pa).

These oils may be hydrocarbon-based oils, silicone oils, or mixtures thereof.

As used herein, the term "hydrocarbon-based oil" means an oil mainly comprising hydrogen and carbon atoms and optionally at least one atom chosen from oxygen, nitrogen, sulphur and phosphorus atoms. The volatile hydrocarbon-based oils may be chosen, for example, from hydrocarbon-based oils comprising from 8 to 16 carbon atoms, such as $C_8$-$C_{16}$ branched alkanes, for instance $C_8$-$C_{16}$ isoalkanes of petroleum origin (also known as isoparaffins), for instance isododecane (also known as 2,2,4,4,6-pentamethylheptane), isodecane and isohexadecane, and, for example, the oils sold under the trade names Isopars or Permetyls, $C_8$-$C_{16}$ branched esters, isohexyl neopentanoate, and mixtures thereof. Other volatile hydrocarbon-based oils, for instance petroleum distillates, such as those sold under the name Shell Solt by the company Shell, may also be used. The volatile solvent is chosen, for example, from hydrocarbon-based volatile oils comprising from 8 to 16 carbon atoms, and mixtures thereof.

Volatile oils which may also be used are volatile silicones such as linear or cyclic volatile silicone oils, for example, those with a viscosity ≦6 centistokes ($6 \times 10^{-6}$ m²/s) comprising, for example, from 2 to 10 silicon atoms, these silicones optionally comprising at least one group chosen from alkyl and alkoxy groups comprising from 1 to 22 carbon atoms. As volatile silicone oils which may be used herein, mention may be made, for example, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The at least one volatile oil may be present in the composition disclosed herein in an amount ranging, for example, from 0.1% to 98% by weight, such as from 1% to 65% by weight, relative to the total weight of the composition.

The composition can also comprise at least one non-volatile oil chosen, for example, from non-volatile hydrocarbon-based oils and silicone oils.

Non-volatile hydrocarbon-based oils that may be mentioned include, for example:

hydrocarbon-based plant oils such as triglycerides comprising fatty acid esters and of glycerol in which the fatty acids may have varied chain lengths from $C_4$ to $C_{24}$, these chains possibly being linear or branched, and saturated or unsaturated; these oils are, for example, wheat germ oil, sunflower oil, grape seed oil, sesame oil, corn oil, apricot oil, castor oil, shea butter, avocado oil, olive oil, soybean oil, sweet almond oil, palm oil, rapeseed oil, cotton oil, hazelnut oil, macadamia oil, jojoba oil, alfalfa oil, poppy oil, pumpkin oil, marrow oil, blackcurrant seed oil, evening primrose oil, millet oil, barley oil, quinoa oil, rye oil, safflower oil, candlenut oil, passion flower oil and musk rose oil; or alternatively caprylic/capric acid triglycerides such as those sold by Stéarineries Dubois or those sold under the names Miglyol 810, 812 and 818 by Dynamit Nobel;

synthetic ethers comprising from 10 to 40 carbon atoms;

linear or branched hydrocarbons of mineral or synthetic origin, such as petroleum jelly, polydecenes, hydrogenated polyisobutene such as parleam, and squalane, and mixtures thereof;

synthetic esters such as oils of formula $R_1COOR_2$ wherein $R_1$ is a fatty acid residue chosen from linear and branched fatty acid residues comprising from 1 to 40 carbon atoms and $R_2$ is a hydrocarbon-based chain chosen, for example, from branched hydrocarbon-based chains comprising from 1 to 40 carbon atoms, provided that the total carbon number of $R_5+R_6 \geqq 10$, for example, purcellin oil (cetostearyl octanoate), isopropyl myristate, isopropyl palmitate, $C_{12}$-$C_{15}$ alkyl, benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, comprising at least one carbon-based chain chosen from branched and/or unsaturated carbon-based chains comprising from 12 to 26 carbon atoms, for instance octyldodecanol, isostearyl alcohol, oleyl alcohol, 2-hexyldecanol, 2-butyloctanol and 2-undecylpentadecanol;

higher fatty acids such as oleic acid, linoleic acid and linolenic acid; and mixtures thereof.

The non-volatile silicone oils which may be used in the composition disclosed herein may be non-volatile polydimethylsiloxanes (PDMSs), polydimethylsiloxanes comprising alkyl or alkoxy groups, that are pendent and/or at the end of a silicone chain, the groups each comprising from 2 to 24 carbon atoms, phenylsilicones, for instance phenyltrimethicones, phenyldimethicones, phenyltrimethylsiloxydiphenylsiloxanes, diphenyldimethicones, diphenylmethyldiphenyltrisiloxanes and 2-phenylethyl trimethylsiloxysilicates.

The non-volatile oils may be present in the composition disclosed herein in an amount ranging, for example, from 0 to 30% (such as from 0.1% to 30%) by weight, further, for example, from 0 to 20% (such as from 0.1% to 20%) by weight and even further, for example, from 0 to 10% (such as from 0.1% to 10%) by weight, relative to the total weight of the composition.

The composition as disclosed herein may also comprise at least one fatty compound that is pasty at room temperature. As used herein, the term "pasty fatty substance" means fatty substances with a melting point ranging from 20 to 55° C., such as from 25 to 45° C., and/or a viscosity at 40° C. ranging from 0.1 to 40 Pa·s (from 1 to 400 poises), such as from 0.5 to 25 Pa·s, measured using a Contraves TV or Rheomat 80 viscometer, equipped with a spindle rotating at 60 Hz. A person skilled in the art can select the spindle for measuring the viscosity from the spindles MS-r3 and MS-r4, on the basis of his general knowledge, so as to be able to carry out the measurement of the pasty compound tested.

These fatty substances are, for example, hydrocarbon-based compounds, optionally of polymeric type; they can also be chosen, for example, from silicone compounds; they may also be in the form of a mixture of hydrocarbon-based compounds and/or silicone compounds. In the case of a mixture of different pasty fatty substances, the hydrocarbon-based pasty compounds (comprising mainly hydrogen and carbon atoms and optionally ester groups) are, for example, used in major proportion.

Among the pasty compounds which may be used in the composition disclosed herein, mention may be made, for example, of lanolins and lanolin derivatives such as acetylated lanolins, oxypropylenated lanolins, and isopropyl lanolate, having a viscosity ranging, for example, from 18 to 21 Pa·s, such as from 19 to 20.5 Pa·s, and/or a melting point ranging from 30 to 55° C., and mixtures thereof. It is also possible to use esters of fatty acids or of fatty alcohols, for example, those comprising from 20 to 65 carbon atoms (with a melting point ranging from 20 to 35° C. and/or viscosity at 40° C. ranging from 0.1 to 40 Pa·s), such as triisostearyl or cetyl citrate; arachidyl propionate; polyvinyl laurate; cholesterol esters, such as triglycerides of plant origin, for example, hydrogenated plant oils, viscous polyesters such as poly(12-hydroxystearic acid), and mixtures thereof.

Mention may also be made, for example, of pasty silicone fatty substances such as polydimethylsiloxanes (PDMSs) comprising pendent chains of the alkyl or alkoxy type comprising from 8 to 24 carbon atoms, and having a melting point of 20-55° C., such as stearyldimethicones, for example, those sold by Dow Corning under the trade names DC2503 and DC25514, and mixtures thereof.

The pasty fatty substance may be present in the composition disclosed herein in an amount ranging, for example, from 0.01% to 60% by weight, such as from 0.5% to 45% by weight, and further such as from 2% to 30% by weight, relative to the total weight of the composition.

The composition as disclosed herein can also comprise at least one emulsifying surfactant, present, for example, in an amount ranging from 2% to 30% by weight, such as from 5% to 15% by weight, relative to the total weight of the composition. The at least one emulsifying surfactant may be chosen from anionic and nonionic surfactants. Reference may be made to "Encyclopedia of Chemical Technology, Kirk-Othmer", volume 22, pp. 333-432, 3rd edition, 1979, Wiley, for the definition of the properties and functions (emulsifying) of surfactants, for example, pp. 347-377 of the reference, for the anionic and nonionic surfactants.

The surfactants used in the composition disclosed herein are chosen, for example, from:
 nonionic surfactants: fatty acids, fatty alcohols, polyethoxylated or polyglycerolated fatty alcohols such as polyethoxylated stearyl or cetylstearyl alcohol, fatty acid esters of sucrose, alkylglucose esters, such as polyoxyethylenated fatty acid esters of $C_1$-$C_6$ alkyl glucose, and mixtures thereof;
 anionic surfactants: $C_{16}$-$C_{30}$ fatty acids neutralized with amines, aqueous ammonia or alkaline salts, and mixtures thereof.

Surfactants that make it possible to obtain an oil-in-water or wax-in-water emulsion are, for example, used.

The composition as disclosed herein can further comprise at least one film-forming polymer.

The at least one film-forming polymer may be present in the composition disclosed herein in a solids content ranging from 0.1% to 60% by weight, such as from 0.5% to 40% by weight and further such as from 1% to 30% by weight, relative to the total weight of the composition.

As used herein, the term "film-forming polymer" means a polymer that is capable, by itself or in the presence of an auxiliary film-forming agent, of forming a continuous and adherent film on a support, for example, on a keratin material such as the eyelashes.

Among the film-forming polymers that may be used in the composition disclosed herein, mention may be made, for example, of synthetic polymers, of radical-mediated type or polycondensate type, and polymers of natural origin, and mixtures thereof.

As used herein, the term "radical-mediated film-forming polymer" means a polymer obtained by polymerization of monomers comprising at least one unsaturation, such as ethylenic unsaturation, wherein each monomer is capable of homopolymerizing (unlike polycondensates).

The film-forming polymers of radical-mediated type may be, for example, vinyl polymers or copolymers, such as acrylic polymers.

The vinyl film-forming polymers can result from the polymerization of monomers comprising at least one ethylenic unsaturation and at least one acidic group and/or esters of these acidic monomers and/or amides of these acidic monomers.

Monomers comprising at least one acidic group which may be used include, for example, α,β-ethylenic unsaturated carboxylic acids such as acrylic acid, methacrylic acid, crotonic acid, maleic acid or itaconic acid. (Meth)acrylic acid and crotonic acid are, for example, used. In one embodiment, (meth)acrylic acid is used.

The esters of acidic monomers are chosen, for example, from (meth)acrylic acid esters (also known as (meth)acrylates), such as (meth)acrylates of an alkyl, for example, a $C_1$-$C_{30}$ alkyl, such as a $C_1$-$C_{20}$ alkyl, (meth)acrylates of an aryl, such as a $C_6$-$C_{10}$ aryl, and (meth)acrylates of a hydroxyalkyl, such as a $C_2$-$C_6$ hydroxyalkyl.

Among the alkyl(meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl(meth)acrylates that may be mentioned, examples include hydroxyethyl acrylate, 2-hydroxypropyl acrylate, hydroxyethyl methacrylate and 2-hydroxypropyl methacrylate.

Among the aryl(meth)acrylates that may be mentioned, examples include benzyl acrylate and phenyl acrylate.

The (meth)acrylic acid esters that may be used are, for example, alkyl (meth)acrylates.

As disclosed herein, the alkyl group of the esters may be either fluorinated or perfluorinated, i.e., some or all of the hydrogen atoms of the alkyl group are substituted with fluorine atoms.

Examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above.

Examples of vinyl esters that may be mentioned include vinyl acetate, vinyl neodecanoate, vinyl pivalate, vinyl benzoate and vinyl t-butylbenzoate.

Styrene monomers that may be mentioned include, for example, styrene and α-methylstyrene.

Among the film-forming polycondensates that may be mentioned, examples include polyurethanes, polyesters, polyesteramides, polyamides, epoxyester resins and polyureas.

The polyurethanes may be chosen from anionic, cationic, nonionic and amphoteric polyurethanes, polyurethane-acrylics, polyurethane-polyvinylpyrrolidones, polyester-polyurethanes, polyether-polyurethanes, polyureas and polyurea/polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid or 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is chosen, for example, from ethylene glycol, diethylene glycol, triethylene glycol, 1,3-propanediol, cyclohexanedimethanol and 4-butanediol. Other polyols that may be used are, for example, glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one group —$SO_3M$, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such a group —$SO_3M$ may, for example, be used.

The aromatic nucleus of the difunctional aromatic monomer also bearing a group —$SO_3M$ as described above may be chosen, for example, from benzene, naphthalene, anthracene, biphenyl, oxybiphenyl, sulphonylbiphenyl and methylenebiphenyl nuclei. Among the difunctional aromatic monomers also bearing a group —$SO_3M$, mention may be made, for example, of: sulphoisophthalic acid, sulphoterephthalic acid, sulphophthalic acid, 4-sulphonaphthalene-2,7-dicarboxylic acid.

The copolymers used are, for example, those based on isophthalate/sulphoisophthalate, such as copolymers obtained by condensation of diethylene glycol, cyclohexanedimethanol, isophthalic acid and sulphoisophthalic acid.

The polymers of natural origin, optionally modified, may be chosen, for example, from shellac resin, sandarac gum, dammar resins, elemi gums, copal resins and cellulose polymers, and mixtures thereof.

In one embodiment, the at least one film-forming polymer may be a water-soluble polymer and may be present in an aqueous phase of the composition; the polymer is thus solubilized in the aqueous phase of the composition. Examples of water-soluble film-forming polymers that may be mentioned include:

proteins, for instance proteins of plant origin such as wheat proteins and soybean proteins; proteins of animal origin such as keratins, for example, keratin hydrolysates and sulphonic keratins;

polymers of cellulose such as hydroxyethylcellulose, hydroxypropylcellulose, methylcellulose, ethylhydroxyethylcellulose and carboxymethylcellulose, and quaternized cellulose derivatives;

acrylic polymers or copolymers, such as polyacrylates or polymethacrylates;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

polymers of natural origin, which are optionally modified, such as:

gum arabics, guar gum, xanthan derivatives, karaya gum;

alginates and carrageenans;

glycosaminoglycans, hyaluronic acid and derivatives thereof;

shellac resin, sandarac gum, dammar resins, elemi gums and copal resins;

deoxyribonucleic acid;

mucopolysaccharides such as chondroitin sulphate, and mixtures thereof.

In another embodiment, the at least one film-forming polymer may be a polymer dissolved in a liquid fatty phase comprising organic solvents or oils such as those described above (in this case, the film-forming polymer is a liposoluble polymer). As used herein, the term "liquid fatty phase" means a fatty phase which is liquid at room temperature (25° C.) and atmospheric pressure (760 mmHg, i.e., $10^5$ Pa), comprising one or more fatty substances that are liquid at room temperature, also known as oils, which are generally mutually compatible.

The liquid fatty phase comprises, for example, a volatile oil, optionally mixed with a non-volatile oil, the oils possibly being chosen from those mentioned above.

Examples of liposoluble polymers which may be used include copolymers of vinyl ester (wherein the vinyl group is directly linked to the oxygen atom of the ester group and the vinyl ester comprises a saturated, linear or branched hydrocarbon-based radical comprising from 1 to 19 carbon atoms, linked to the carbonyl of the ester group) and of at least one other monomer which may be a vinyl ester (other than the vinyl ester already present), an α-olefin (comprising from 8 to 28 carbon atoms), an alkyl vinyl ether (in which the alkyl group comprises from 2 to 18 carbon atoms) or an allylic or methallylic ester (comprising a saturated, linear or branched hydrocarbon-based radical comprising from 1 to 19 carbon atoms, linked to the carbonyl of the ester group).

These copolymers may be crosslinked with the aid of crosslinking agents, which may be either of the vinyl type or the allylic or methallylic type, such as tetraallyloxyethane, divinylbenzene, divinyl octanedioate, divinyl dodecanedioate and divinyl octadecanedioate.

Examples of these copolymers which may be used include the following copolymers:
vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetaallyloxyethane, vinyl acetate/al lyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of liposoluble film-forming polymers which may also be used include liposoluble copolymers, such as those resulting from the copolymerization of vinyl esters comprising from 9 to 22 carbon atoms or of alkyl acrylates or methacrylates, wherein the alkyl radical comprises from 10 to 20 carbon atoms.

Such liposoluble copolymers may be chosen, for example, from polyvinyl stearate, polyvinyl stearate crosslinked with the aid of divinylbenzene, of diallyl ether or of diallyl phthalate, polystearyl(meth)acrylate, polyvinyl laurate and polylauryl(meth)acrylate, it being possible for these poly(meth)acrylates to be crosslinked with the aid of ethylene glycol dimethacrylate or tetraethylene glycol dimethacrylate.

The liposoluble copolymers disclosed above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) such as copolymers of vinylpyrrolidone and of $C_2$ to $C_{40}$ such as $C_3$ to $C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

The at least one film-forming polymer may also be present in the composition in the form of particles dispersed in an aqueous phase or in a non-aqueous solvent phase, which is generally known as a latex or pseudolatex. The techniques for preparing these dispersions are well known to those skilled in the art.

Aqueous dispersions of film-forming polymers which may be used are, for example, the acrylic dispersions sold under the names Neocryl XK-90®, Neocryl A-1070®, Neocryl A-1090®, Neocryl BT-62®, Neocryl A-1079® and Neocryl A-523® by the company Avecia-Neoresins, Dow Latex 432® by the company Dow Chemical, Daitosol 5000 AD® by the company Daito Kasey Kogyo; or the aqueous dispersions of polyurethane sold under the names Neorez R-981® and Neorez R-974® by the company Avecia-Neoresins, Avalure UR-405®, Avalure UR-410®, Avalure UR-425®, Avalure UR-450®, Sancure 875®, Sancure 861®, Sancure 878® and Sancure 2060® by the company-Goodrich, Impranil 85® by the company Bayer and Aquamere H-1511® by the company Hydromer; the sulphopolyesters sold under the brand name "Eastman AQ®" by the company Eastman Chemical Products, vinyl dispersions, for instance "Mexomer PAM" and also acrylic dispersions in isododecane, for instance "Mexomer PAP" by the company Chimex.

The composition as disclosed herein may further comprise at least one plasticizer, which promotes the formation of a film with the film-forming polymer. Such a plasticizer may be chosen from any of the compounds known to those skilled in the art as being capable of satisfying the desired function.

Additives

The composition as disclosed herein may also comprise at least one dyestuff chosen, for example, from pulverulent dyestuffs, liposoluble dyes and water-soluble dyes. The at least one dyestuff may be present in an amount ranging, for example, from 0.01% to 30% by weight relative to the total weight of the composition.

The pulverulent dyestuffs may be chosen, for example, from pigments and nacres.

The pigments may be white or colored, mineral and/or organic, and coated or uncoated. Among the mineral pigments which may be used, examples include titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments that may be used, examples include carbon black, pigments of D & C type, and lakes based on cochineal carmine or on barium, strontium, calcium or aluminium.

The nacres may be chosen, for example, from white nacreous pigments such as mica coated with titanium or with bismuth oxychloride, colored nacreous pigments such as titanium mica with iron oxides, titanium mica with, such as ferric blue or chromium oxide, titanium mica with an organic pigment of the above mentioned type, and nacreous pigments based on bismuth oxychloride.

The liposoluble dyes include, for example, Sudan Red, D&C Red 17, D&C. Green 6, β-carotene, soybean oil, Sudan Brown, D&C Yellow 11, D&C Violet 2, D&C Orange 5, quinoline yellow and annatto. The water-soluble dyes include, for example, beetroot juice, methylene blue, the disodium salt of ponceau, the disodium salt of alizarin green, quinoline yellow, the trisodium salt of amaranthus, the disodium salt of tartrazine, the monosodium salt of rhodamine, the disodium salt of fuchsin, and xanthophyll.

The composition as disclosed herein may also comprise at least one additive chosen from those commonly used in cosmetics, such as antioxidants, fillers, preserving agents, fragrances, neutralizers, thickeners and vitamins, and mixtures thereof.

The fillers may be chosen from those that are well known to a person skilled in the art and commonly used in cosmetic compositions. The fillers may be mineral or organic and lamellar or spherical. Among the fillers that may be used herein, mention may be made, for example, of talc, mica, silica, kaolin, polyamide powder for instance Nylon® (Orgasol® from Atochem), poly-β-alanine powder and polyethylene powder, tetrafluoroethylene polymer powders for instance Teflon®, lauroyllysine, starch, boron nitride, expanded hollow polymer microspheres such as those made of polyvinylidene chloride/acrylonitrile, for instance Expancel® (Nobel Industrie), acrylic powders such as Polytrap® (Dow Corning), polymethyl methacrylate particles and silicone resin microbeads (for example Tospearls® from Toshiba), precipitated calcium carbonate, magnesium carbonate, magnesium hydrocarbonate, hydroxyapatite, hollow silica microspheres (Silica Beads® from Maprecos), glass or ceramic microcapsules, and metal soaps derived from organic carboxylic acids comprising from 8 to 22 carbon atoms such as from 12 to 18 carbon atoms, for example zinc, magnesium or lithium stearate, zinc laurate or magnesium myristate.

The fillers may be present in an amount ranging, for example, from 0.1% to 25% by weight, such as from 1% to 20% by weight, relative to the total weight of the composition.

In one embodiment, the composition disclosed herein is a mascara.

A person skilled in the art will take care to select the optional additional additives and/or the amount thereof such that the advantageous properties of the composition disclosed herein are not, or are not substantially, adversely affected by the addition envisaged.

The composition disclosed herein may be manufactured by the known processes generally used in cosmetics.

The composition disclosed herein may be packaged in an applicator assembly comprising a reservoir and a removable tool for closing the reservoir, such as in a leaktight manner.

The applicator assembly may also comprise an applicator member for applying the makeup composition to the keratin fibers, such as the eyelashes, wherein the applicator member allows the composition to be taken up and allow the composition taken up to be deposited on the eyelashes. This applicator member is, for example, securely fastened to the tool for leaktight closure of the assembly.

The applicator assembly may also comprise a draining member (or drainer) for the applicator member, wherein the draining member is possibly securely fastened to the reservoir.

The applicator member may, for example, be a mascara brush that is well known to those skilled in the art. Such a brush comprises, for example, bristles arranged radially around a twisted core, such as a metal core. The brush may be of varied shape and may comprise cutout sections. Mascara brushes are described, for example, in documents FR-A-2 607 373, EP-A-611 170, EP-A-811 336, EP-A-811 337 and EP-A-842 620.

FIG. 1 shows one embodiment of a packaging and applicator assembly 1 comprising a composition for coating keratin fibers as disclosed herein.

The packaging and applicator assembly 1 comprises a container 2 on which is mounted a threaded neck 3, one free edge of which delimits an aperture 4. In the aperture 4 is mounted a draining member 5. The assembly 1 also comprises an applicator device 10 comprising a cap 11 securely fastened to a stem 13, one end of which comprises an applicator 12, generally configured in the form of an arrangement of fibers held between the two branches of a twisted iron wire. An inner surface of the cap 11 is threaded so as to engage with the threading of the neck 3. Thus, when the applicator 12 and the stem 13 are placed inside the container 2, the threading of the cap 11 engages with the threading of the neck 3 such that the cap closes the aperture 4 of the container in a leaktight manner.

Alternatively, the applicator may comprise a comb generally comprising a plurality of teeth obtained by moulding with a support made of thermoplastic material. The applicator may also comprise a comb combined with a brush.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The examples that follow are given as non-limiting illustrations of the present disclosure.

EXAMPLE 1

A wax-in-water emulsion mascara comprising the composition below was prepared:

| | |
|---|---|
| Tacky wax (Kester Wax K 82 P from Koster Keunen) | 25 g |
| Candellila wax | 5 g |
| Amino-2 methyl-2 propanediol-1,3 | 0.5 g |
| Triethanolamine | 2.4 g |
| Stearic acid | 5.8 g |
| Hydroxyethylcellulose | 0.9 g |
| Silica | 1 g |
| Arabic gum | 3.4 g |
| Polyimide-amide fibers (2 mm, 2.2 Dtex) (KERMEL TECH from Rhodia) | 1 g |
| Pigments | 5.5 g |
| Preservatives | qs |
| Water | qsp 100 g |

This mascara was judged as forming a smooth and uniform makeup on eyelashes, and also as giving a volumizing and lengthening effect.

EXAMPLE 2

The following wax-in-water emulsion mascara was prepared:

| | |
|---|---|
| Tacky wax (Kester Wax K 82 P from Koster Keunen) | 25 g |
| Candellila wax | 3 g |
| Amino-2 methyl-2 propanediol-1,3 | 0.5 g |
| Triethanolamine | 2.4 g |
| Stearic acid | 5.8 g |
| Hydroxyethylcellulose | 0.9 g |
| Silica | 1 g |
| Arabic gum | 3.4 g |
| Cellulose fibers (1.3 mm) (Rayon Flock Rcise N0003 MO4 from Claremont Flock Corporation) | 1 g |
| Pigments | 5.5 g |
| Preservatives | qs |
| Water | qsp 100 g |

EXAMPLE 3

A wax-in-water emulsion mascara comprising the composition below was prepared:

| | |
|---|---|
| Tacky wax (Kester Wax K 82 P from Koster Keunen) | 25 g |
| Candellila wax | 6 g |
| Isononyl isononanoate | 3 g |
| Amino-2 methyl-2 propanediol-1,3 | 0.5 g |
| Triethanolamine | 2.4 g |
| Stearic acid | 5.8 g |
| Hydroxyethylcellulose | 0.9 g |
| Silica | 1 g |
| Arabic gum | 3.4 g |
| Polyimide-amide fibers (2 mm, 2.2 Dtex) (KERMEL TECH from Rhodia) | 0.5 g |
| Pigments | 5.5 g |
| Ethylic alcohol | 3 g |
| Preservatives | qs |
| Water | qsp 100 g |

EXAMPLE 4

An anhydrous mascara comprising the composition below was prepared:

| | |
|---|---|
| Tacky wax (Kester Wax K 82 P from Koster Keunen) | 35 g |
| Vinyl acetate/allyl stearate copolymer (Mexomere PQ ® from CHIMEX) | 2.2 g |
| Vinyl polylaurate (Mexomere PP ® from CHIMEX) | 0.75 g |
| Talc | 0.8 g |
| Bentone | 5.3 g |
| Propylene carbonate | 1.7 g |
| Pigments | 4.6 g |
| Polyimide-amide fibers (2 mm, 2.2 Dtex) (KERMEL TECH from Rhodia) | 1 g |
| Preservatives | qs |
| Isododecane | qsp 100 g |

EXAMPLE 5

The following anhydrous mascara was prepared:

| | |
|---|---|
| Tacky wax (Kester Wax K 82 P from Koster Keunen) | 35 g |
| Vinyl acetate/allyl stearate copolymer (Mexomere PQ ® from CHIMEX) | 2.2 g |
| Vinyl polylaurate (Mexomere PP ® from CHIMEX) | 0.75 g |
| Talc | 0.8 g |
| Bentone | 5.3 g |
| Propylene carbonate | 0.5 g |
| Pigments | 4.6 g |
| Polyamide fibers (3 mm, 0.9 Dtex) (Polyamide 6.6 0.9 Dtex, 3.0 mm from Paul Bonte) | 1 g |
| Preservatives | qs |
| Isododecane | qsp 100 g |

EXAMPLE 6

The following anhydrous mascara was prepared:

| | |
|---|---|
| Tacky wax (Kester Wax K 82 P from Koster Keunen) | 30 g |
| Vinyl acetate/allyl stearate copolymer (Mexomere PQ ® from CHIMEX) | 2.2 g |
| Vinyl Polylaurate (Mexomere PP ® from CHIMEX) | 0.75 g |
| Talc | 0.8 g |
| Bentone | 5.3 g |
| Propylene carbonate | 1.7 g |
| Pigments | 4.6 g |
| Polyimide-amide fibers (2 mm, 2.2 Dtex) (KERMEL TECH from Rhodia) | 1 g |
| Preservatives | qs |
| Isododecane | qsp 100 g |

This mascara was judged as forming a smooth and uniform makeup on eyelashes, and also as giving a volumizing and lengthening effect.

What is claimed is:

1. A composition for coating keratin fibers, comprising, in a cosmetically acceptable medium, at least one tacky wax with a tack of greater than or equal to 0.7 N.s, and fibers, wherein:

the at least one tacky wax is chosen from $C_{20}$-$C_{40}$ alkyl (hydroxystearoyloxy)stearates;

the at least one tacky wax is present in an amount ranging from 0.5% to 65% by weight, relative to the total weight of the composition;

the fibers are rigid fibers chosen from aromatic polyimide-amide fibers, wherein the aromatic polyimide-amide is obtained by polymerization of tolylene diisocyanate and trimellitic anhydride, and comprises repeating units of formula:

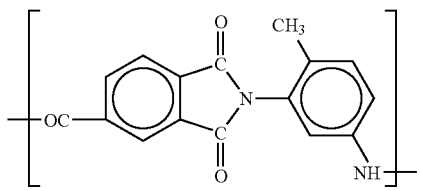

obtained by polycondensation of tolylene diisocyanate and trimellitic anhydride; and the fibers are present in an amount ranging from 0.5% to 10% by weight, relative to the total weight of the composition.

2. The composition according to claim 1, wherein the at least one tacky wax has a tack ranging from 0.7 N.s to 30 N.s.

3. The composition according to claim 2, wherein the at least one tacky wax has a tack ranging from 2 N.s to 10 N.s.

4. The composition according to claim 1, wherein the at least one tacky wax has a hardness of less than or equal to 3.5 MPa.

5. The composition according to claim 4, wherein the at least one tacky wax has a hardness ranging from 0.1 MPa to 2.5 MPa.

6. The composition according to claim 1, wherein the at least one tacky wax is present in an amount ranging from 10% to 40% by weight, relative to the total weight of the composition.

7. The composition according to claim 1, wherein the fibers have a length ranging from 1 μm to 10 mm.

8. The composition according to claim 1, wherein the fibers have a cross section that is within a circle of diameter ranging from 2 nm to 500 μm.

9. The composition according to claim 1, comprising an aqueous phase.

10. The composition according to claim 9, wherein the aqueous phase comprises water or a mixture of water and at least one water-miscible organic solvent.

11. The composition according to claim 10, wherein the at least one water-miscible organic solvent is chosen from lower monoalcohols comprising from 1 to 5 carbon atoms, glycols comprising from 2 to 8 carbon atoms, $C_3$-$C_4$ ketones and $C_2$-$C_4$ aldehydes.

12. The composition according to claim 9, wherein the aqueous phase is present in an amount ranging from 1% to 95% by weight, relative to the total weight of the composition.

13. The composition according to claim 1, further comprising at least one volatile oil.

14. The composition according to claim 13, wherein the at least one volatile oil is chosen from hydrocarbon-based oils and silicone oils.

15. The composition according to claim 13, wherein the at least one volatile oil is present in an amount ranging from 0.1% to 98% by weight, relative to the total weight of the composition.

16. The composition according to claim 1, further comprising at least one non-volatile oil.

17. The composition according to claim 16, wherein the at least one non-volatile oil is present in an amount ranging from 0.1% to 30% by weight, relative to the total weight of the composition.

18. The composition according to claim 1, further comprising at least one film-forming polymer.

19. The composition according to claim 18, wherein the at least one film-forming polymer is present in a solids content ranging from 0.1% to 60% by weight, relative to the total weight of the composition.

20. The composition according to claim 1, further comprising at least one additional wax.

21. The composition according to claim 20, wherein the at least one additional wax is present in an amount ranging from 0.1% to 50% by weight, relative to the total weight of the composition.

22. The composition according to claim 1, further comprising at least one surfactant.

23. The composition according to claim 1, further comprising at least one additive chosen from dyestuffs, antioxidants, fillers, pasty fatty substances, preserving agents, fragrances, neutralizers, thickeners, vitamins, coalescers and plasticizers, and mixtures thereof.

24. The composition according to claim 1, wherein the composition is a mascara.

* * * * *